(12) United States Patent
Lee et al.

(10) Patent No.: US 11,957,415 B2
(45) Date of Patent: Apr. 16, 2024

(54) METHOD AND DEVICE FOR OPTIMIZING SURGERY

(71) Applicant: HUTOM CO., LTD., Seoul (KR)

(72) Inventors: Jong Hyuck Lee, Seongnam-si (KR); Hoon Mo Yang, Gunpo-si (KR); Ho Seung Kim, Yongin-si (KR)

(73) Assignee: HUTOM CO., LTD., Seoul (KR)

( * ) Notice: Subject to any disclaimer, the term of this patent is extended or adjusted under 35 U.S.C. 154(b) by 879 days.

(21) Appl. No.: 16/997,044

(22) Filed: Aug. 19, 2020

(65) Prior Publication Data

US 2020/0375662 A1 Dec. 3, 2020

Related U.S. Application Data

(63) Continuation of application No. PCT/KR2019/002088, filed on Feb. 20, 2019.

(30) Foreign Application Priority Data

Feb. 20, 2018 (KR) .......... 10-2018-0019866
Feb. 20, 2018 (KR) .......... 10-2018-0019867
(Continued)

(51) Int. Cl.
*A61B 34/10* (2016.01)
*A61B 34/30* (2016.01)
*G06N 20/00* (2019.01)

(52) U.S. Cl.
CPC .......... *A61B 34/10* (2016.02); *A61B 34/30* (2016.02); *G06N 20/00* (2019.01);
(Continued)

(58) Field of Classification Search
CPC ... A61B 34/10; A61B 34/30; A61B 2034/102; A61B 2034/107; A61B 2034/301; G06N 20/00
See application file for complete search history.

(56) References Cited

U.S. PATENT DOCUMENTS

2003/0109780 A1* 6/2003 Coste-Maniere ..... G06T 7/0012
600/407
2009/0017430 A1 1/2009 Muller-Daniels et al.
(Continued)

FOREIGN PATENT DOCUMENTS

CN 106901834 A 6/2017
EP 3252737 A1 12/2017
(Continued)

OTHER PUBLICATIONS

Office Action issued in KR 10-2018-0027818; mailed by the Korean Intellectual Property Office dated Apr. 30, 2018.
(Continued)

*Primary Examiner* — Kibrom K Gebresilassie
(74) *Attorney, Agent, or Firm* — Studebaker & Brackett PC

(57) ABSTRACT

A surgery optimizing method performed by a computer is provided. The method includes generating a plurality of genes corresponding to a surgical procedure based on the surgical procedure composed of at least one detailed surgical operation, performing virtual surgery on each of the plurality of genes to evaluate whether surgery is optimized, selecting at least one gene among the plurality of genes based on the evaluation result to apply a genetic algorithm, and applying the genetic algorithm to generate a new gene and deriving an optimal surgical procedure based on the new gene.

9 Claims, 11 Drawing Sheets

(30) Foreign Application Priority Data

| Feb. 20, 2018 | (KR) | ........................ 10-2018-0019868 |
| Mar. 9, 2018 | (KR) | ........................ 10-2018-0027818 |
| Sep. 27, 2018 | (KR) | ........................ 10-2018-0115328 |
| Nov. 15, 2018 | (KR) | ........................ 10-2018-0140771 |

(52) U.S. Cl.
CPC ... *A61B 2034/102* (2016.02); *A61B 2034/107* (2016.02); *A61B 2034/301* (2016.02)

(56) References Cited

U.S. PATENT DOCUMENTS

| 2014/0057236 A1* | 2/2014 | Meglan | ................. G09B 23/30 434/274 |
| 2017/0007327 A1* | 1/2017 | Haider | ................. A61B 90/36 |
| 2019/0307510 A1* | 10/2019 | Rotenberg | ............. G06T 17/00 |

FOREIGN PATENT DOCUMENTS

| IT | 20090470 A1 | 1/2011 |
| JP | 2008-173159 A | 7/2008 |
| JP | 2013-511355 A | 4/2013 |
| KR | 10-2010-0106834 A | 10/2010 |
| KR | 10-2012-0046439 A | 5/2012 |
| KR | 10-1152177 B1 | 6/2012 |
| KR | 10-1206340 B1 | 11/2012 |
| KR | 10-2014-0035035 A | 3/2014 |
| KR | 10-1700847 B1 | 1/2017 |
| WO | 2011/040769 A2 | 4/2011 |
| WO | 2015/095715 A1 | 6/2015 |

OTHER PUBLICATIONS

International Search Report issued in PCT/KR2019/002088; dated May 28, 2019.

The extended European search report issued by the European Patent Office dated Jan. 26, 2022, which corresponds to European Patent Application No. 119756860.3-1126 and is related to U.S. Appl. No. 16/997,044.

Communication pursuant to Article 94(3) EPC issued by the European Patent Office dated Oct. 27, 2022, which corresponds to European Patent Application No. 19756860.3-1126 and is related to U.S. Appl. No. 16/997,044.

* cited by examiner

METHOD AND DEVICE FOR OPTIMIZING SURGERY

CROSS-REFERENCE TO RELATED APPLICATIONS

The present application is a continuation of International Patent Application No. PCT/KR2019/002088, filed on Feb. 20, 2019, which is based upon and claims the benefit of priority to Korean Patent Application Nos. 10-2018-0019866, 10-2018-0019867, 10-2018-0019868 filed on Feb. 20, 2018, 10-2018-0027818 filed on Mar. 9, 2018, 10-2018-0115328 filed on Sep. 27, 2018 and 10-2018-0140771 filed on Nov. 15, 2018. The disclosures of the above-listed applications are hereby incorporated by reference herein in their entirety.

BACKGROUND

Embodiments of the inventive concept described herein relate to a method and device for optimizing surgery.

Recently, the research for applying virtual reality to a medical surgery simulation field has been actively conducted.

Medical surgery may be classified into Minimally Invasive Surgery (MIS) including open surgery, laparoscopic surgery, and robot surgery, radio surgery, or the like. The open surgery refers to surgery performed by medical staff that directly watches and touches an area to be treated; the MIS is also called "keyhole surgery", and typically includes laparoscopic surgery and robot surgery. The laparoscopic surgery makes a small hole in the required portion without opening, inserts laparoscopic with a special camera and surgical instruments into a body, and performs microsurgery using lasers or special instruments while observing the body through a video monitor. In addition, the robot surgery is to perform MIS using a surgical robot. Furthermore, the radio surgery refers to the treatment of surgery with radiation or laser light from outside a body.

Conventionally, when the laparoscopic surgery or the robot surgery is performed, after the keyhole corresponding to the entry position is set to the general position, surgery has been performed. Because the surgical instrument enters the general position without reflecting the patient's physical condition (e.g., organ placement characteristics inside a body and body surface appearance), the length of a surgical instrument, the degree of freedom of a surgical instrument, or the like, the surgical operation may not be performed properly inside the body. Moreover, surgery is performed in MIS by entering a surgical instrument and a camera inside a patient's body, and thus the surgical instrument may not be suitable for movement due to the internal structure of the body.

Also, in the case of medical surgery such as the above-described MIS, surgery needs to be performed using accurate operations and suitable tools during actual surgery. Accordingly, there is a need to provide an optimized surgical method for performing surgery using accurate operations and suitable tools.

SUMMARY

Embodiments of the inventive concept provide a method and device for optimizing surgery.

Embodiments of the inventive concept provide a method and device for deriving an optimized surgical procedure using a genetic algorithm.

Embodiments of the inventive concept provide a method and device for providing a surgical procedure consisting of the optimized detailed surgical operation by applying a genetic algorithm to a surgical procedure consisting of a detailed surgical operation.

Embodiments of the inventive concept provide a method and device for providing an optimized surgical instrument.

Embodiments of the inventive concept provide a method and device for providing an optimal entry position of a surgical instrument.

Embodiments of the inventive concept provide a method and device for deriving the structure of a surgical instrument for performing an optimized surgical operation without restrictions due to the constraints in an internal space of a patient's body or the characteristics of a surgical instrument.

Embodiments of the inventive concept provide a method and device for calculating an optimal entry position of a surgical instrument, which improves efficiency and convenience in actual surgery of medical staff by calculating one or more entry positions optimized to perform an surgical operation on a patient's surgical portion based on the results of a surgery simulation, after a part (operation part) of the surgical instrument displayed on a screen during laparoscopic surgery or robot surgery is implemented in a virtual body model.

The technical problems to be solved by the present inventive concept are not limited to the aforementioned problems, and any other technical problems not mentioned herein will be clearly understood from the following description by those skilled in the art to which the inventive concept pertains.

According to an exemplary embodiment, a surgery optimizing method performed by a computer includes generating a plurality of genes corresponding to a surgical procedure based on the surgical procedure composed of at least one detailed surgical operation, performing virtual surgery on each of the plurality of genes to evaluate whether surgery is optimized, selecting at least one gene among the plurality of genes based on the evaluation result to apply a genetic algorithm, and applying the genetic algorithm to generate a new gene and deriving an optimal surgical procedure based on the new gene.

According to an exemplary embodiment, an optimized surgical instrument providing method performed by a computer includes obtaining a virtual body model generated to be matched with a body state of a surgical subject, simulating a surgical operation within the virtual body model, using a surgical instrument, and deriving a configuration of the surgical instrument suitable to apply a surgical operation performed by the surgical instrument in an inner body space of the surgical subject based on the simulation result.

According to an exemplary embodiment, an optimal entry position providing method of a surgical instrument performed by a computer includes obtaining a virtual body model generated to be matched with a body state of a surgical subject, performing simulation using an operation unit of a surgical instrument for performing a surgical operation on a surgical target site of the surgical subject in the virtual body model, and calculating an optimal entry position on a body surface of the surgical subject, to which the surgical operation performed by the operation unit is capable of being applied in an inner body space of the surgical subject based on the simulation result.

According to an exemplary embodiment, an optimized surgical instrument providing method performed by a computer includes obtaining a virtual body model generated to be matched with a body state of a surgical subject, simulating a surgical operation corresponding to an actual surgical operation of the surgical subject in the virtual body model, and deriving a surgical instrument or surgical robot suitable to apply the surgical operation in an inner body space of the surgical subject based on the simulation result.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
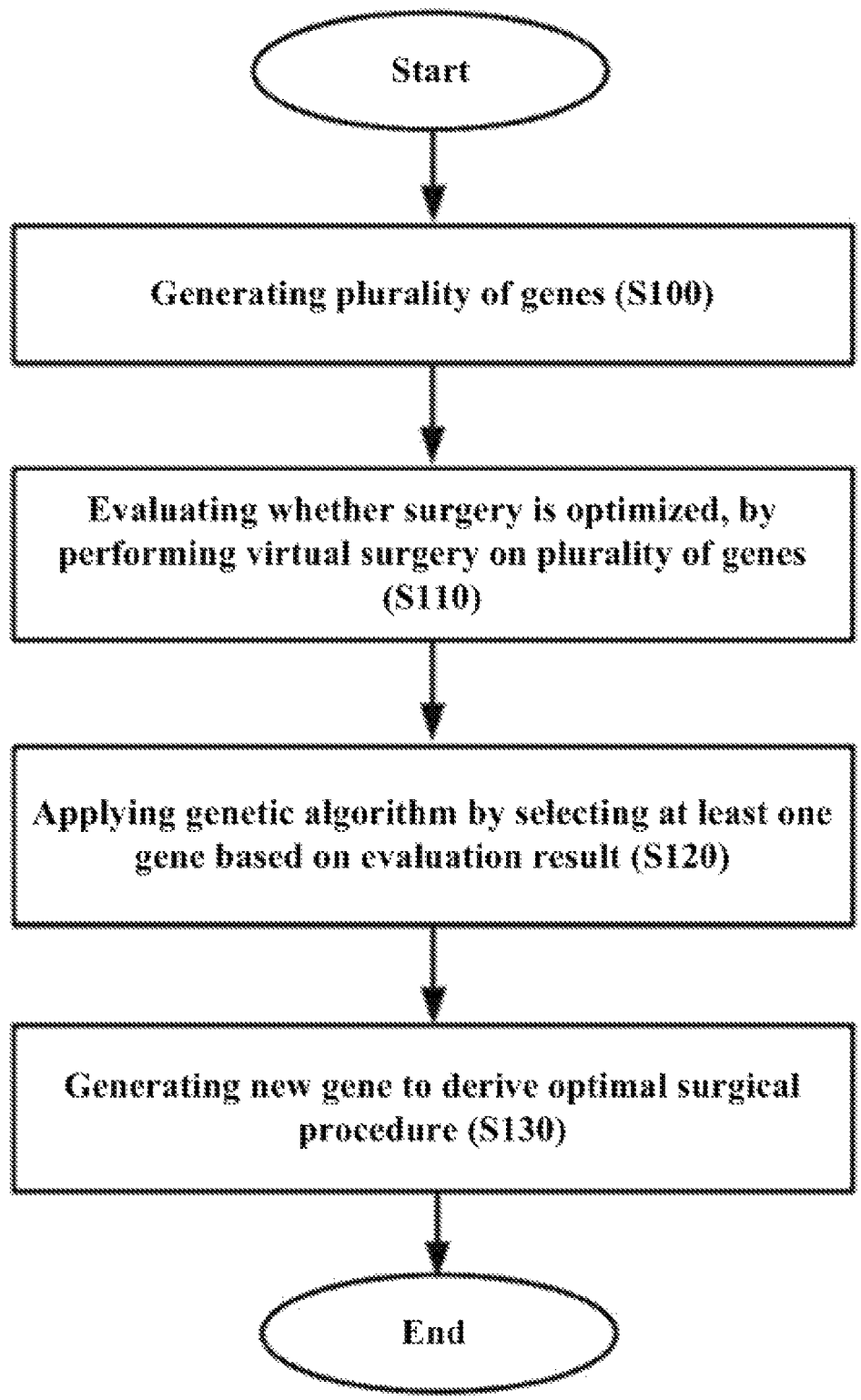
FIG. 1 is a flowchart illustrating a method for optimizing surgery according to an embodiment of the inventive concept.

The above and other aspects, features and advantages of the inventive concept will become apparent from the following description of the following embodiments given in conjunction with the accompanying drawings. The inventive concept, however, may be embodied in various different forms, and should not be construed as being limited only to the illustrated embodiments. Rather, these embodiments are provided as examples so that the inventive concept will be thorough and complete, and will fully convey the concept of the inventive concept to those skilled in the art. The inventive concept may be defined by scope of the claims. Meanwhile, the terminology used herein to describe embodiments of the inventive concept is not intended to limit the scope of the inventive concept.

The terminology used herein is for the purpose of describing embodiments and is not intended to limit the inventive concept. In the specification, the singular forms include plural forms unless particularly mentioned. The terms "comprises" and/or "comprising" used herein does not exclude presence or addition of one or more other elements, in addition to the aforementioned elements. The same reference numerals denote the same elements throughout the specification. As used herein, the term "and/or" includes any and all combinations of one or more of the associated components. It will be understood that, although the terms "first", "second", etc., may be used herein to describe various components, these components should not be limited by these terms. These terms are only used to distinguish one component from another component. Thus, a first component discussed below could be termed a second component without departing from the teachings of the inventive concept.

Unless otherwise defined, all terms (including technical and scientific terms) used herein have the same meaning as commonly understood by those skilled in the art to which the inventive concept pertains. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein.

The term "unit" or "module" used herein may refer to software or hardware such as field programmable gate array (FPGA) or application specific integrated circuit (ASIC), and the "unit" or "module" may perform some functions. However, the "unit" or "module" may be not limited to software or hardware. The "unit" or "module" may be configured to exist in an addressable storage medium or may be configured to execute one or more processors. Therefore, as an example, "units" or "module" may include various elements such as software elements, object-oriented software elements, class elements, and task elements, processes, functions, attributes, procedures, subroutines, program code segments, drivers, firmware, microcodes, circuits, data, databases, data structures, tables, arrays, and variables. Functions provided in "units" or "modules" and elements may be combined into a smaller number of "units" or "modules" and elements or may be divided into additional "units" or "modules" and elements.

Hereinafter, a method and device for optimizing surgery according to an embodiment of the inventive concept will be described in detail with reference to FIGS. 1 to 6.

In this specification, a 'computer' includes all various devices capable of providing results to a user by performing arithmetic processing. For example, the computer may correspond to not only a desktop personal computer (PC) or a notebook but also a smart phone, a tablet PC, a cellular phone, a personal communication service phone (PCS phone), a mobile terminal of a synchronous/asynchronous International Mobile Telecommunication-2000 (IMT-2000), a palm PC, a personal digital assistant (PDA), and the like. Besides, when the head mounted display (HMD) device includes a computing function, the HMD device may be a computer. Furthermore, the computer may correspond to a server that receives a request from a client and processes information.

In this specification, a "gene" may be a concept corresponding to a solution to a problem used in a genetic algorithm. That is, the "gene" may be a concept corresponding to a single surgical procedure in a genetic algorithm procedure used to derive an optimal surgical procedure. For example, the "gene" may be expressed using surgical cue sheet data composed of at least one detailed surgical operation. In addition, the "gene" may be reconstructed into surgical cue sheet data composed of detailed surgical operations optimized as an evolution process is performed by a genetic algorithm.

In this specification, the "detailed surgical operation" may mean a minimum operation unit constituting a surgical process.

In this specification, the "surgical cue sheet data" may be data composed of at least one detailed surgical operation, as data recording a specific surgical procedure.

Hereinafter, embodiments of the inventive concept will be described in detail with reference to accompanying drawings.

FIG. 1 is a flowchart illustrating a method for optimizing surgery according to an embodiment of the inventive concept.

For convenience of description, the method of FIG. 1 is described as being performed by a computer; however, the subject of each operation is not limited to a specific device; the method of FIG. 1 may be used as the meaning including a device capable of performing computing processing. That is, in an embodiment, the computer may refer to a device capable of performing a method for optimizing surgery according to an embodiment of the inventive concept.

Referring to FIG. 1, the surgery optimization method according to an embodiment of the inventive concept may include generating (S100) a plurality of genes corresponding to the surgical procedure based on a surgical procedure composed of at least one detailed surgical operation, evaluating (S110) whether the surgery is optimized, by performing virtual surgery on each of the plurality of genes, applying (S120) a genetic algorithm by selecting at least one gene among a plurality of genes based on the evaluation result, and generating (S130) a new gene by applying a genetic algorithm, and deriving an optimal surgical procedure based on the new gene. Hereinafter, the detailed description of each operation is provided.

A computer may generate a plurality of genes corresponding to the surgical procedure based on a surgical procedure composed of at least one detailed surgical operation (S100).

In an embodiment, the computer may obtain surgical cue sheet data configured to include at least one detailed surgical operation, and may generate a first gene based on the obtained surgical cue sheet data. Besides, the computer may generate a second gene by obtaining other surgical cue sheet data, and may repeat this process to generate a plurality of genes.

The detailed surgical operation refers to a minimum operation unit constituting the surgical process, and may be, for example, the minimum unit of the surgical operation divided depending on specific criteria in the surgical process. For example, the detailed surgical operation may be generated by dividing the surgical operation into minimum units based on the type of surgery (e.g., laparoscopic surgery, robot surgery, surgery using endoscopy, or the like), an anatomical body part where surgery is performed, surgical instruments used during surgery, the number of surgical instruments, the direction or location of a surgical instrument on a screen, the movement (e.g., forward/retreat, or the like) of a surgical instrument, and the like. Accordingly, the detailed surgical operation may include at least one of surgical type information, surgical operation type information, surgical site information, and surgical instrument information.

The surgical cue sheet data may be composed of at least one detailed surgical operation as data recording a specific surgical procedure. For example, the surgical cue sheet data may be obtained by sequentially listing one complete surgical procedure arranged with detailed surgical operations.

The detailed surgical operation and the surgical cue sheet data composed of detailed surgical operation may be generated based on actual surgery data obtained in an actual surgical procedure. For example, medical staff may perform surgery directly on a patient or perform MIS using a surgical robot, a laparoscope, an endoscope, or the like. Various pieces of information (i.e., actual surgery data) about surgical operation performed in the surgical procedure, a surgical instrument associated with the surgical operation, a surgical site, or the like may be obtained. For example, the surgery image data obtained by capturing a surgical procedure focused on the surgical site may be obtained as actual surgery data; data recorded for the surgical operation performed in the surgical procedure may be obtained as actual surgery data. Moreover, the detailed surgical operation and the surgical cue sheet data composed of detailed surgical operation may be generated based on virtual surgery data obtained by performing virtual surgery (e.g., surgery simulation). For example, the virtual surgery data may be image data obtained by performing a virtual surgery on a patient using a simulator, and may be data recorded for a surgical operation performed in a virtual surgical procedure.

As described above, the computer may obtain the surgical cue sheet data generated based on actual surgery data or virtual surgery data, and may generate a gene corresponding to the obtained surgical cue sheet data.

As described above, a gene may be a concept corresponding to a solution to a problem used in a genetic algorithm; in an embodiment of the inventive concept, a single surgical procedure may be expressed as a single gene. That is, the gene may be data indicating a surgical procedure composed of at least one detailed surgical operation.

Figure 2:
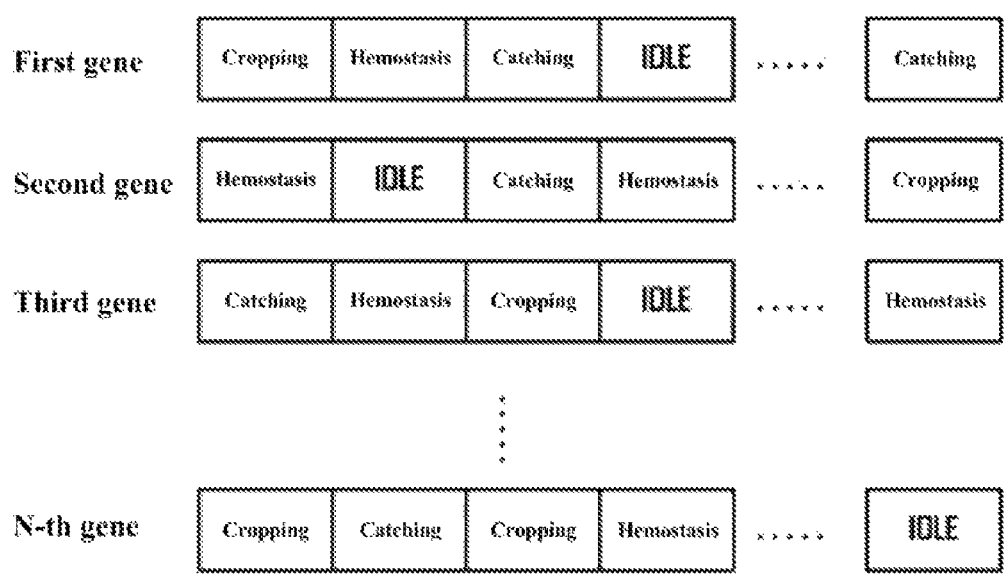
FIG. 2 is a diagram illustrating a process of generating a gene according to an embodiment of the inventive concept.

FIG. 2 is a diagram illustrating a process of generating a gene according to an embodiment of the inventive concept.

Referring to FIG. 2, a computer may generate a single gene (i.e., surgical cue sheet data) corresponding to a single specific surgical procedure. That is, the computer may generate a first gene corresponding to the first surgical procedure (i.e., first surgical cue sheet data), and a second gene corresponding to the second surgical procedure (i.e., second surgical cue sheet data). Accordingly, the computer may generate 'n' genes by repeating this process 'n' times. At this time, 'n' genes may be generated in a random manner. In addition, each of the 'n' genes may be composed of a single completed surgical procedure.

For example, as illustrated in FIG. 2, when the first surgical procedure is composed of 'm' detailed surgical operations such as cropping, hemostasis, catching, and the like, the computer obtains the first surgical cue sheet data configured to list the 'm' detailed surgical operations in order, and may generate the first gene, by constructing the first surgical cue sheet data into a specific data type (e.g., bit string) for indicating the gene.

Returning to FIG. 1, the computer may perform virtual surgery on each of a plurality of genes to evaluate whether the surgery is optimized (S110).

In an embodiment, the computer may perform virtual surgery on each of a plurality of genes based on a detailed surgical operation in the surgical cue sheet data. The computer may calculate the fitness value for each gene through the virtual surgery for each of a plurality of genes, and may evaluate whether surgery corresponding to each gene is optimized surgery, based on the fitness value.

Upon performing virtual surgery for each gene, each gene may be generated based on the surgical cue sheet data composed of detailed surgical operations, and thus the computer may perform virtual surgery depending on the detailed surgical operation in each gene. For example, because the detailed surgical operation is data including surgical type information (e.g., information such as laparoscopic surgery, robot surgery, surgery using endoscopy), surgical operation type information (e.g., information such as cropping, hemostasis, catching, or the like), surgical site information (information about the location, type, or the like of a specific surgical site, where surgery is performed, such as organs, blood vessels, tissues or the like in the body), and surgical instrument information (e.g., information about the number, type, direction, location, movement, or the like of a surgical instrument), the computer may realize the surgical procedure corresponding to each gene, using information in this detailed surgical operation.

Upon calculating the fitness value for each gene, the computer may calculate a fitness value, using at least one of information about whether surgery is successful, information associated with surgery time, and information associated with a surgical instrument. The computer may use the optimization objective function to derive the optimal solution as a result of virtual surgery on each gene; at this time, the computer may calculate the fitness value for the gene, using the information about whether surgery is successful, the information associated with surgery time, and the information associated with a surgical instrument as variables of the optimization objective function.

In an embodiment, the computer may calculate the fitness value, using the optimization objective function as illustrated in Equation 1 below.

$$F(x)=s\{w_1(1-b)+w_2L(A)+w_3c+w_4d+w_5a\}$$ [Equation 1]

Herein, 'x' may be information composed of a bit string including surgical cue sheet data, as a gene.

$w_1$ to $w_4$ may be weights, and may be determined based on the importance or the like of each variable through, for example, learning.

's' may be information indicating whether surgery is successful; for example, '0' may indicate failure, and '1' may indicate success.

'b' may be "(total bleeding time)/(total surgery time)".

L(A) may be "1/(sum of the total distance moved by surgical instruments in set A)".

'c' may be "1/(number of cuts)".

'd' may be "1/(total surgery time)".

'A' may be a set having all surgical instruments used in surgery as elements; for example, 'A' may be a set of "{tool 1, tool 2, tool 3 . . . }".

'a' may be "1/n(A)", or "1/(total number of surgical instruments used in surgery)".

According to Equation 1, the computer may evaluate surgery, which needs to succeed, and in which total surgery time is short, a bleeding time is short, the distance of a surgical instrument is short, the number of cuts is small, and the number of used surgical instruments is small, as optimized surgery. That is, the computer may calculate variables of the optimization objective function as in Equation 1, by performing virtual surgery on each gene, and finally, may calculate fitness values for genes by substituting each variable into Equation 1.

The fitness value may be determined depending on the features desired to be evolved. Equation 1 above is only one example for calculating the fitness value; factors such as whether surgery is successful, information associated with surgery time (e.g., total surgery time or bleeding time), information associated with a surgical instrument (e.g., the number of surgical instruments or a movement distance), and surgical operation information (e.g., the number of cuts, or the like) may be changed depending on what the optimized target surgery is.

The computer may select at least one gene evaluated as optimized surgery among a plurality of genes based on the evaluation result in step S110 to apply a genetic algorithm to the selected at least one gene (S120).

In an embodiment, the computer may select at least one gene having the fitness value matched with a predetermined condition among a plurality of genes, based on the fitness value of each gene calculated to evaluate whether the surgery is optimized. For example, the computer may set selecting a gene with the fitness value not less than a specific reference value, as a condition; the computer may set selecting a gene with the highest fitness value, as a condition. Afterward, the computer may apply a genetic algorithm to the selected gene depending on the predetermined condition. For example, the genetic algorithms such as selection, crossover, mutation, and replacement may be applied.

Figure 3A:
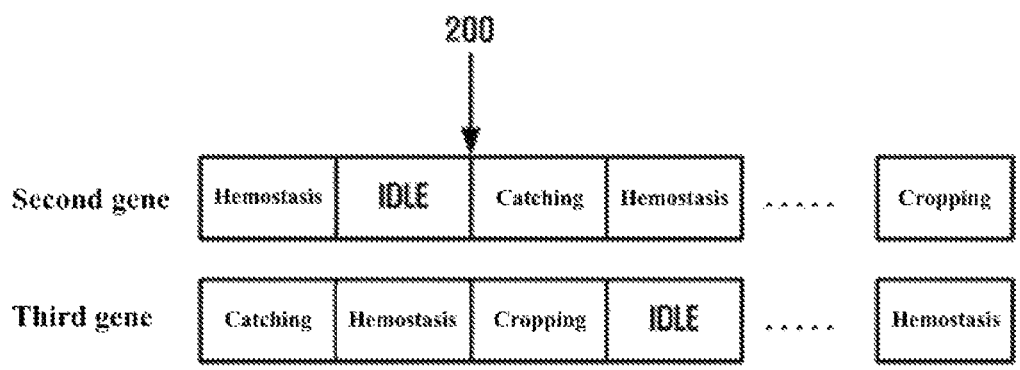
FIGS. 3A and 3B are diagrams illustrating a process of crossing a gene, as an example of applying a genetic algorithm, according to an embodiment of the inventive concept.
Figure 3B:
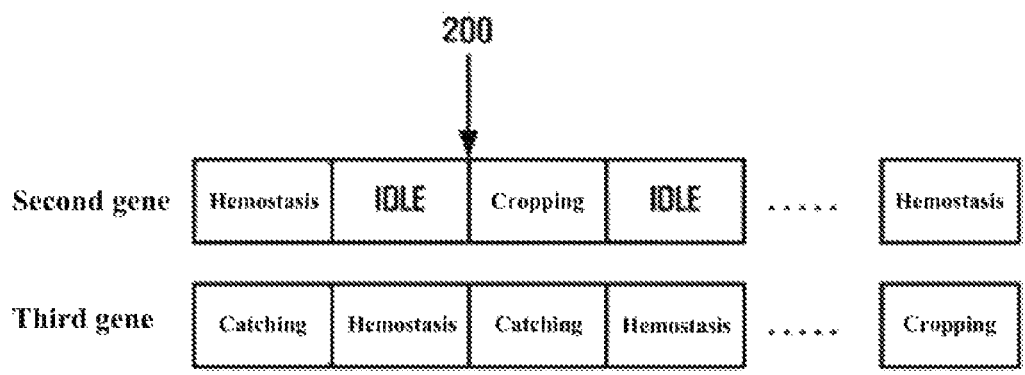

FIGS. 3A and 3B are diagrams illustrating a process of crossing a gene, as an example of applying a genetic algorithm, according to an embodiment of the inventive concept.

In an embodiment, a computer may generate 'n' genes as illustrated in FIG. 2 and may perform virtual surgery on each of the 'n' genes to calculate the fitness value (e.g., the fitness value using Equation 1) of each gene. The computer may select a gene having the greatest fitness value among 'n' genes or a gene having a fitness value not less than a specific reference value, based on the fitness value calculated for each of the 'n' genes. At this time, the method of selecting a gene may vary depending on which condition is set.

For example, when two genes (e.g., the second gene and the third gene) having the fitness value (e.g., the largest fitness value) matched with a condition among 'n' genes are selected, the computer may cross two genes (e.g., the second gene and the third gene).

Referring to FIG. 3A, the computer may set a specific point 200 for crossing the second gene and third gene, and may cross the second gene and third gene based on the set specific point 200.

Referring to FIG. 3B, as a result of crossover with the third gene, the second gene may be replaced with detailed surgical operations of the third gene based on the specific point 200. Besides, as a result of crossover with the second gene, the third gene may be replaced with detailed surgical operations of the second gene based on the specific point 200.

The specific point 200 for the crossover between genes may be selected randomly. At this time, as the specific point 200, a single point may be used, or a plurality of points may be used. Furthermore, the specific point 200 may be selected identically for each gene, or may be differently selected.

When the gene crossover process is repeated 'n' times, the total of '2n' new genes may be generated. In an embodiment, the computer may determine the number of gene crossover processes depending on how much the computer evolves (changes) genes. For example, the computer may repeat the gene crossover process in consideration of the number of genes generated initially; when the number of initially-generated genes (parent genes) is 'n', the computer may generate 'n' new genes (child genes) by performing the gene crossover process n/2 times.

Figure 4:
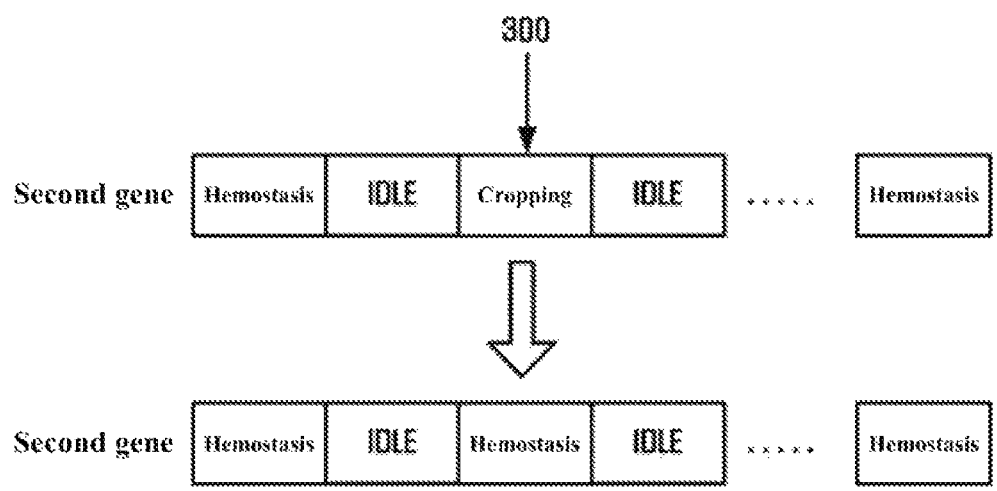
FIG. 4 is a diagram illustrating a process of mutating a gene, as an example of applying a genetic algorithm, according to an embodiment of the inventive concept.

FIG. 4 is a diagram illustrating a process of mutating a gene, as an example of applying a genetic algorithm, according to an embodiment of the inventive concept.

In an embodiment, a computer may generate 'n' genes as illustrated in FIG. 2 and may perform virtual surgery on each of the 'n' genes to calculate the fitness value (e.g., the fitness value using Equation 1) of each gene. The computer may select a gene having the greatest fitness value among 'n' genes or a gene having a fitness value not less than a specific reference value, based on the fitness value calculated for each of the 'n' genes. At this time, the method of selecting a gene may vary depending on which condition is set.

For example, when one gene (e.g., the second gene) having the fitness value (e.g., the largest fitness value) matched with a condition among 'n' genes is selected, the computer may apply a mutation genetic algorithm to the selected one gene (e.g., the second gene).

Referring to FIG. 4, the computer may select a specific point 300 for mutate the second gene, and may change the gene (e.g., the detailed surgical operation of cropping) corresponding to the selected specific point 300 to another gene (e.g., the detailed surgical operation of hemostasis).

The specific point 300 for mutating a gene may be selected randomly. In an embodiment, the specific point 300 may be selected using probability. For example, the computer may set a probability value P (e.g., P is a small value such as 0.001, or the like); the computer may generate a random value, using a random function at the position (i.e., each detailed surgical operation in the gene) of the gene, and then may compare the random value with the probability P. The computer may select a gene matched with a condition (e.g., a probability value less than P) as the specific point 300 (i.e., the detailed surgical operation). Besides, as the specific point 300, a single point may be used, or a plurality of points may be used.

Returning to FIG. 1, the computer may generate a new gene (child gene) by applying a genetic algorithm to the initial genes (parent genes) generated in step S100, and may derive the optimal surgical procedure based on the new gene (S130).

In an embodiment, as described above, the computer may generate at least one new gene (child gene) by applying the genetic algorithm such as crossover, mutation, or the like to genes (parent genes) that have been initially generated. At this time, the computer may repeatedly perform step S110 to step S120 on the new gene (child gene). At this time, the number of repetitions may be determined in advance.

For example, a computer may perform virtual surgery on a new gene (child gene) to calculate a fitness value. Furthermore, the computer may determine whether the fitness value of the new gene (child gene) is matched with a predetermined condition. The computer may select a new gene (child genes) matched with the condition to apply the genetic algorithm such as crossover, mutation, or the like to the selected new gene. A new child gene may be generated again by applying the genetic algorithm to the new gene (child gene). In other words, the computer repeatedly generates child genes from parent genes, based on the results of fitness value for evaluating whether surgery is optimized, and then may obtain a gene including the optimal surgical procedure among the finally-generated child genes. For example, the computer may select the gene with the highest fitness value among child genes and may derive the gene through an optimized surgical procedure.

At this time, whenever the genetic process such as step S110 to step S120 is repeatedly performed, only the genes with a high fitness value are selected and then continuously evolved, and thus child genes have a higher fitness value than the parent genes. That is, child genes may be composed of detailed surgical operations consisting of surgical procedures more improved than parent genes. Accordingly, the computer may select a gene having the highest fitness value from the finally-generated child genes and may obtain the optimized surgical cue sheet data from the selected gene. At this time, the optimized surgical cue sheet data includes detailed surgical operation information composed of the optimized surgical procedures in terms of surgical time, an operation of surgical tools, the number of used surgical tools, the prognosis of surgery, or the like.

As described above, according to an embodiment of the inventive concept, it is possible to derive an improved surgical procedure compared to the surgical process performed in the actual surgical procedure, by applying a genetic algorithm.

Furthermore, according to an embodiment of the inventive concept, surgical cue sheet data including the optimized surgical procedure may be derived through a genetic algorithm, and thus the surgical cue sheet data may be provided to actual medical staff. In addition, actual medical staff may utilize the optimized surgical cue sheet data during actual surgery, thereby performing accurate surgical operations and surgical procedures.

Also, according to an embodiment of the inventive concept, surgical cue sheet data including the optimized surgical procedure may be derived through a genetic algorithm, and thus the surgical cue sheet data may be used as learning data in a learning process such as deep learning.

Figure 5:
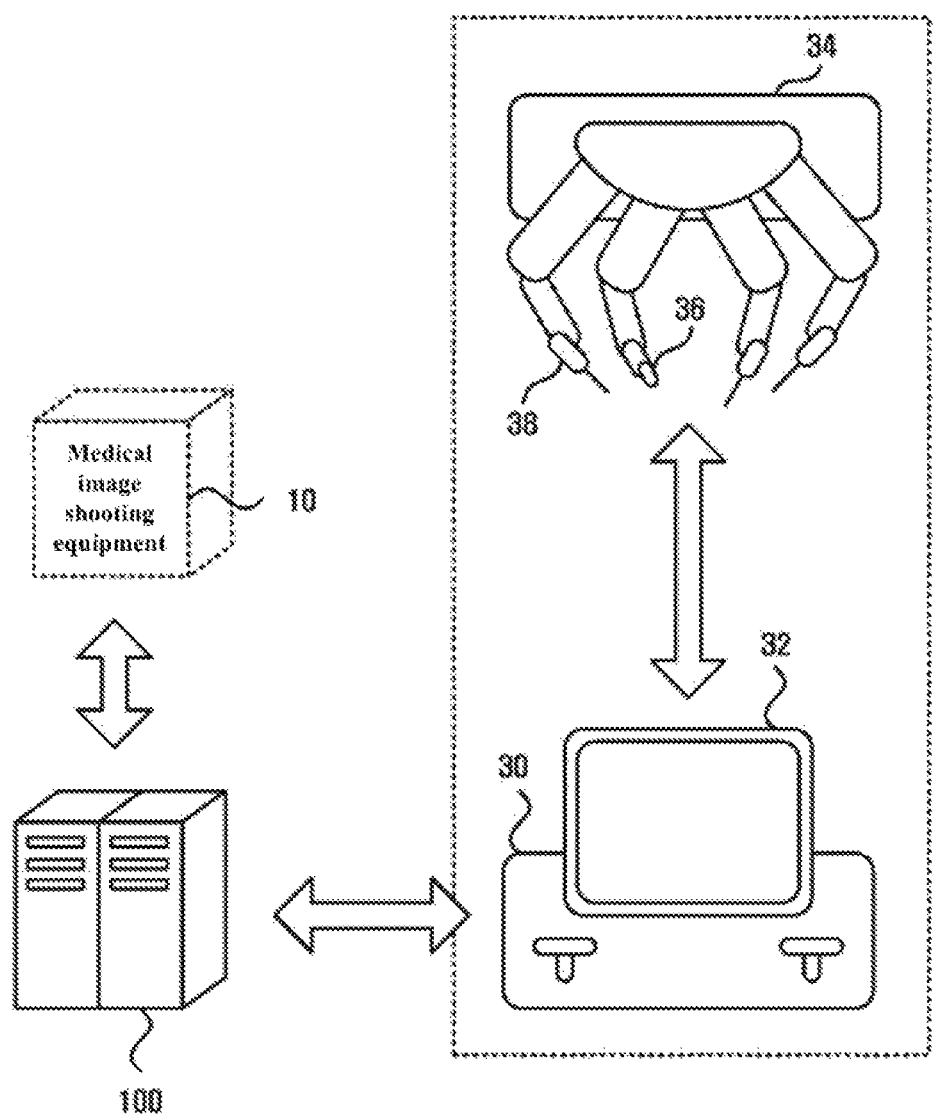
FIG. 5 is a schematic diagram of a system capable of performing robot surgery according to an embodiment of the inventive concept.

FIG. 5 is a schematic diagram of a system capable of performing robot surgery according to an embodiment of the inventive concept.

Referring to FIG. 5, the robot surgery system includes a medical image shooting equipment 10, a controller 30 provided in a server 100 and an operating room, a display 32, a surgical robot 34. According to an embodiment, the medical image shooting equipment 10 may be omitted in the robot surgery system according to the disclosed embodiment.

In an embodiment, the surgical robot 34 includes a shooting device 36 and a surgical instrument 38.

In an embodiment, a user controls the robot 34 for surgery, using the controller 30, and thus robot surgery is performed. In an embodiment, the robot surgery may be automatically performed by the controller 30 without the control of the user.

The server 100 is a computing device including at least one processor and a communication unit.

The controller 30 includes the computing device including the at least one processor and the communication unit. In an embodiment, the controller 30 includes hardware and software interfaces for controlling the surgical robot 34.

The shooting device 36 includes at least one image sensor. That is, the shooting device 36 is used to photograph an object, that is, a surgical site, by including at least one camera device. In an embodiment, the shooting device 36 includes at least one camera coupled with the surgical arm of the surgical robot 34.

In an embodiment, the image captured by the shooting device 36 is displayed on the display 32.

In an embodiment, the surgical robot 34 includes one or more surgical instruments 38 capable of performing cutting, clipping, fixing, catching operations, or the like of a surgical site. The surgical instrument 38 is used in combination with the surgical arm of the surgical robot 34.

The controller 30 receives information necessary for surgery from the server 100 or generates information necessary for surgery and provides the information to the user. For example, the controller 30 displays the generated-or-received information necessary for surgery on the display 32.

For example, the user operates the controller 30 while watching the display 32, controls the movement of the surgical robot 34, and thus performs robot surgery.

The server 100 generates information necessary for robot surgery, using medical image data of an object previously photographed from the medical image shooting equipment 10, and provides the generated information to the controller 30.

The controller 30 provides information to the user by displaying information received from the server 100 on the display 32; alternatively, the controller 30 controls the surgical robot 34, using information received from the server 100.

In an embodiment, the means capable of being used in the medical image shooting equipment 10 is not limited; for example, various other medical image acquisition means such as CT, X-Ray, PET, and MRI may be used.

As described above, when robot surgery is performed, data including various pieces of surgical information may be obtained from the surgical image taken in the surgical procedure or the control process of the surgical robot. In an embodiment, in the inventive concept, the surgical cue sheet data described above may be composed based on the surgical information (i.e., surgical image) obtained from the robot surgical procedure, and a gene may be generated from the surgical cue sheet data. In addition, in the inventive concept, an optimized surgical procedure (i.e., an optimized surgical cue sheet data) as described in the embodiments of FIGS. 1 to 4 may be derived and applied to the robot surgical procedure of FIG. 5. In this case, the surgical robot may perform surgery depending on the optimized surgical cue sheet data, and thus the surgery may be performed more accurately and effectively.

Figure 6:
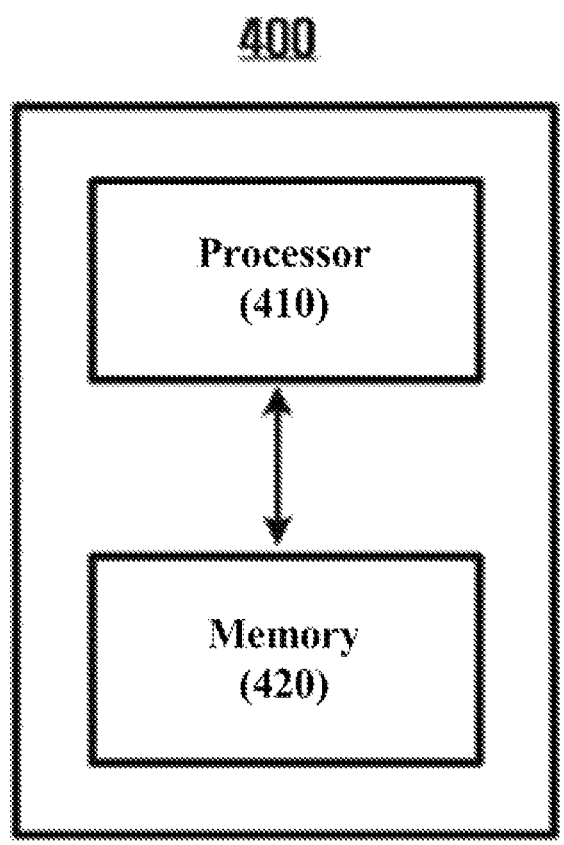
FIG. 6 is a block diagram schematically illustrating a configuration of a device 400 performing a surgery optimizing method according to an embodiment of the inventive concept.

FIG. 6 is a block diagram schematically illustrating a configuration of a device 400 performing a surgery optimizing method according to an embodiment of the inventive concept.

Referring to FIG. 6, a processor 410 may include one or more cores (not illustrated), a graphic processing unit (not illustrated), and/or a connection path (e.g., a bus, or the like) through which a signal is transmitted and received with other components.

According to an embodiment, the processor 410 may perform a surgical image providing method described with reference to FIGS. 1 to 4 by executing one or more instructions stored in a memory 420.

For example, the processor 410 may execute one or more instructions stored in the memory 420; and thus the processor 410 may generate a plurality of genes based on the detailed surgical operation, may evaluate whether surgery is optimized by performing virtual surgery on each of a plurality of genes, may select at least one gene among a plurality of genes based on the evaluation results to apply a genetic algorithm to the selected at least one gene, may generate a new gene by applying a genetic algorithm, and may derive the optimal surgical procedure based on the new gene.

In the meantime, the processor 410 may further include Random Access Memory (RAM) (not illustrated) and Read-Only Memory (ROM) (not illustrated) that temporarily and/or permanently store a signal (or data) processed inside the processor 410. Furthermore, the processor 410 may be implemented in the form of a system on chip (SoC) including at least one of a graphic processor, RAM, and ROM.

Programs (one or more instructions) for the processing and controlling of the processor 410 may be stored in the memory 420. The programs stored in the memory 420 may be divided into a plurality of modules depending on functions.

The surgery optimizing method according to an embodiment of the inventive concept may be implemented by a program (or an application) and may be stored in a medium such that the program is executed in combination with a computer being hardware.

Hereinafter, a method and device for providing a surgical instrument according to an embodiment of the inventive concept will be described in detail with reference to FIGS. 7 to 11.

In this specification, a 'computer' includes all various devices capable of providing results to a user by performing arithmetic processing. For example, the computer may correspond to not only a desktop personal computer (PC) or a notebook but also a smart phone, a tablet PC, a cellular phone, a personal communication service phone (PCS phone), a mobile terminal of a synchronous/asynchronous International Mobile Telecommunication-2000 (IMT-2000), a palm PC, a personal digital assistant (PDA), and the like. Besides, when the head mounted display (HMD) device includes a computing function, the HMD device may be a computer. Furthermore, the computer may correspond to a server that receives a request from a client and processes information.

Hereinafter, embodiments of the inventive concept will be described in detail with reference to accompanying drawings.

Figure 7:
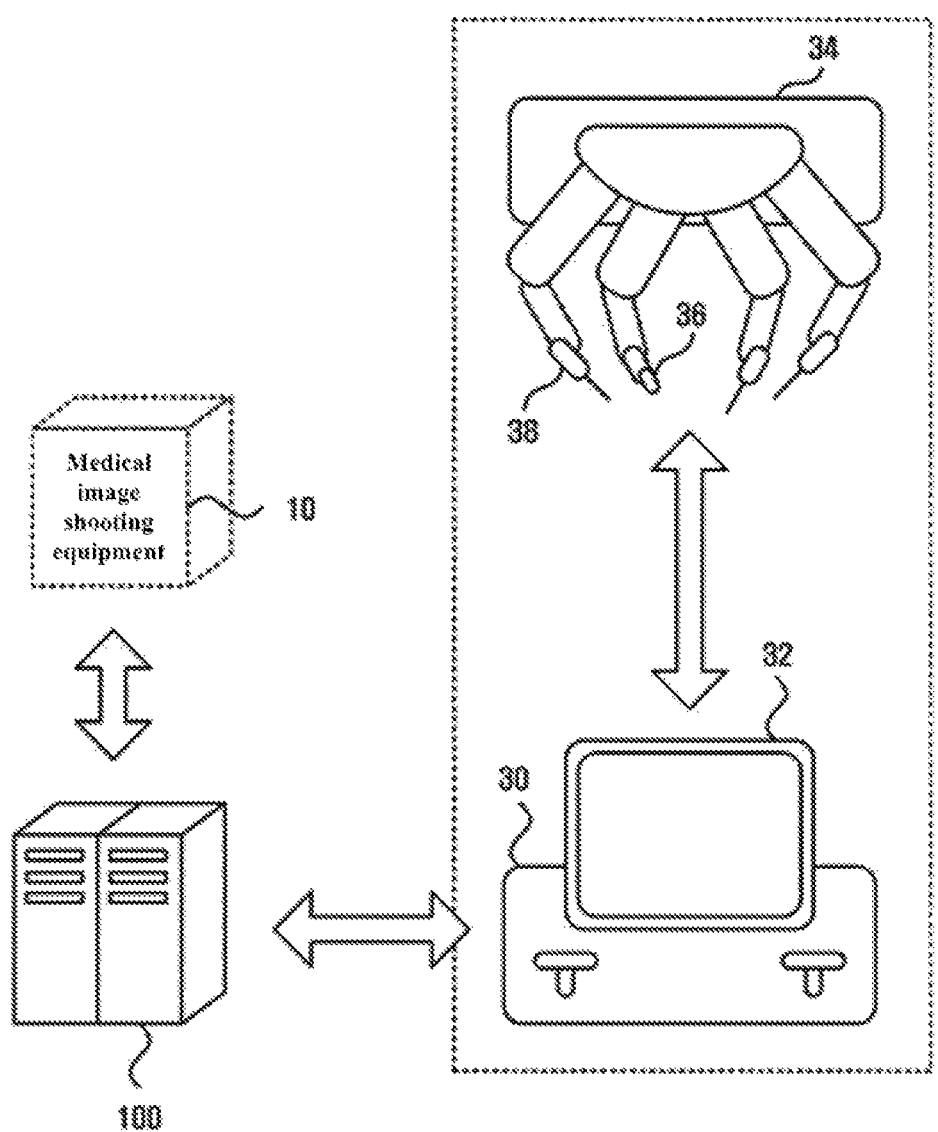
FIG. 7 is a schematic diagram of a system capable of performing robot surgery according to an embodiment of the inventive concept.

FIG. 7 is a schematic diagram of a system capable of performing robot surgery according to an embodiment of the inventive concept.

Referring to FIG. 7, the robot surgery system includes the medical image shooting equipment 10, the server 100, the controller 30, the display 32, the surgical robot 34 provided in an operating room. According to an embodiment, the medical image shooting equipment 10 may be omitted in the robot surgery system according to the disclosed embodiment.

In an embodiment, the surgical robot 34 includes the shooting device 36 and the surgical instrument 38.

In an embodiment, a user controls the robot 34 for surgery, using the controller 30, and thus robot surgery is performed. In an embodiment, the robot surgery may be automatically performed by the controller 30 without the control of the user.

The server 100 is a computing device including at least one processor and a communication unit.

The controller 30 includes the computing device including the at least one processor and the communication unit. In an embodiment, the controller 30 includes hardware and software interfaces for controlling the surgical robot 34.

The shooting device 36 includes at least one image sensor. That is, the shooting device 36 is used to photograph an object, that is, a surgical site, by including at least one camera device. In an embodiment, the shooting device 36 includes at least one camera coupled with the surgical arm of the surgical robot 34.

In an embodiment, the image captured by the shooting device 36 is displayed on the display 32.

In an embodiment, the surgical robot 34 includes one or more surgical instruments 38 capable of performing cutting, clipping, fixing, catching operations, or the like of a surgical site. The surgical instrument 38 is used in combination with the surgical arm of the surgical robot 34.

The controller 30 receives information necessary for surgery from the server 100 or generates information necessary for surgery and provides the information to the user. For example, the controller 30 displays the generated-or-received information necessary for surgery on the display 32.

For example, the user operates the controller 30 while watching the display 32, controls the movement of the surgical robot 34, and thus performs robot surgery.

The server 100 generates information necessary for robot surgery, using medical image data of an object previously photographed from the medical image shooting equipment 10, and provides the generated information to the controller 30.

The controller 30 provides information to the user by displaying information received from the server 100 on the display 32; alternatively, the controller 30 controls the surgical robot 34, using information received from the server 100.

In an embodiment, the means capable of being used in the medical image shooting equipment 10 is not limited; for example, various other medical image acquisition means such as CT, X-Ray, PET, and MRI may be used.

In the case of MIS, such as the robot surgery, laparoscopic surgery, or surgery using an endoscope, the surgery is performed by entering a surgical instrument and a camera into the body (i.e., a surgical site) of a patient (i.e., the subject of surgery). In this case, organs, blood vessels, and the like are arranged inside the patient's body; because a space inside the body is narrow, and thus it is not easy to perform a surgical operation by inserting a surgical instrument. Accordingly, in the inventive concept, the occurrence of limitations in surgical procedures due to the placement of organs, blood vessels, and the like that are inside a patient's body, or the length of a surgical instrument, the structure of a surgical instrument, or the like may be minimized, and it is possible to provide medical staff with a method for performing the most convenient surgical operation. Hereinafter, it will be described in detail.

Figure 8:
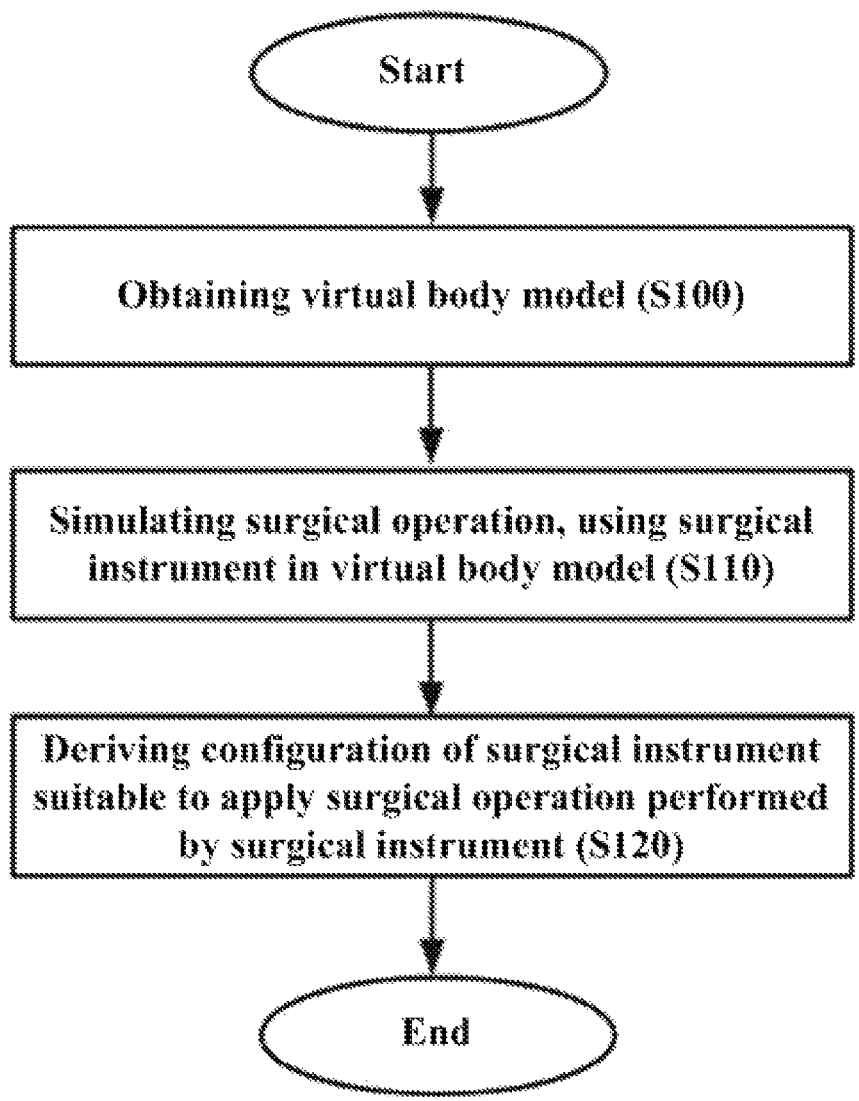
FIG. 8 is a flowchart schematically illustrating a method for providing an optimized surgical instrument according to an embodiment of the inventive concept.

FIG. 8 is a flowchart schematically illustrating a method for providing an optimized surgical instrument according to an embodiment of the inventive concept.

Each of the steps illustrated in FIG. 8 may be performed in a time-series manner in the server 100 or controller 30 illustrated in FIG. 7. Alternatively, each of the steps may be performed in a computing device provided separately. Hereinafter, for convenience of description, each step may be described as being performed by a computer. However, the subject of each step is not limited to a specific device. All or part of steps may be performed by the server 100 or the controller 30, or may be performed on a separately-provided computing device.

Referring to FIG. 8, a method for providing an optimized surgical instrument performed by a computer according to an embodiment of the inventive concept may include obtaining a virtual body model generated to be matched with the body state of a surgical subject (S100), simulating a surgical operation using a surgical instrument in a virtual body model (S110), and deriving a configuration of a surgical instrument suitable to apply a surgical operation performed by a surgical instrument in a space inside the body of the surgical subject based on the simulation result (S120). Hereinafter, the detailed description of each operation is provided.

The computer may obtain a virtual body model generated to be matched with the body state of a surgical subject (S100).

The virtual body model may be 3D modeling data generated based on medical image data (e.g., the medical image captured through CT, PET, MRI, or the like) captured of the body of the surgical subject in advance. For example, the virtual body model may be modeled to be matched with the body of the surgical subject, and may be corrected to the same state as the actual surgical state.

The medical staff may perform rehearsal or simulation, using a virtual body model implemented in the same way as the body state of the surgical subject, and thus the medical staff may experience the same state as a state in actual surgery. At this time, the medical staff may freely perform the surgical operation in the space inside the patient's body through the virtual body model. For example, virtual surgery may be performed depending on the surgical operation pattern of the medical staff without the limitations according to the internal feature of the patient's body (e.g., an organ placement, a vascular state, or the like) or the feature of a surgical instrument. Moreover, after the virtual surgery is performed, it is possible to derive the optimal actual surgical procedure in consideration of the internal feature of the patient's body, the feature of the surgical instrument, or the like based on the results. Also, when the virtual surgery using the virtual body model is performed, data including a rehearsal or simulation action for the virtual body model may be obtained. For example, image data obtained by performing the virtual surgery (i.e., rehearsal or simulation) on the virtual body model may be obtained, or data obtained by recording the surgical operation performed on the virtual body model may be obtained.

The computer may simulate a surgical operation, using a surgical instrument in the virtual body model (S110).

The surgical instrument may be configured to include an operation unit directly performing a surgical operation on a surgical site and an arm part that is connected to the operation unit to operate. For example, the operation unit may be a part that may access a surgical site to perform a surgical operation such as capturing, cropping, moving, or suturing a target object, and may be composed of various instruments depending on the purpose of the surgical operation. The arm part may be connected to the operation unit to operate depending on the movement of the operation unit, or may operate to control the movement of the operation unit.

In the case of MIS, such as robot surgery or laparoscopic surgery in FIG. 7, only the operation unit of the surgical instrument may be captured by the camera inserted into the body of the surgical subject and may be visible through a screen. Accordingly, the operation state of the arm part of the surgical instrument is not provided through the screen.

In an embodiment, the computer may simulate the surgical operation, using only the operation unit of the surgical instrument within the virtual body model. That is, the computer may perform simulation by implementing only the operation unit generating a change in the space inside the virtual body model among the configurations of the surgical instrument (e.g., physically or chemically changing organs, blood vessels, tissues, or the like in the body, or providing an external object such as clips, gauze, saline, and the like in the space inside the virtual body model). Accordingly, in such the simulation, virtual surgery may be performed using only the operation unit of the surgical instrument in the virtual body model without considering whether the internal organs of the body is affected, the entry position on the patient's body surface, or the like depending on the feature of the arm part of the surgical instrument or the operation of the arm part, thereby applying the easiest and most familiar surgical operation pattern.

Here, the simulation (virtual surgery) for the virtual body model may be performed by medical staff, or may be performed by the computer itself. When the simulation (virtual surgery) is performed by the medical staff, the computer receives the manipulation of a controller by the medical staff. Furthermore, when the computer performs the simulation by itself, the computer may perform virtual surgery on a specific patient, based on the result of learning the conventional surgical data.

The computer may derive a configuration of a surgical instrument suitable to apply a surgical operation performed by a surgical instrument in a space inside the body of the surgical subject based on the simulation results (S120).

In particular, the computer may obtain the motion information of the surgical instrument based on the simulation results through the virtual body model. The motion information may be information indicating a position change of the surgical instrument generated as a surgical operation is performed; for example, the motion information may be the set of coordinate values indicating the position of each point of the surgical instrument on coordinates of the virtual body model. In addition, the computer may derive a configuration of a surgical instrument suitable to apply the motion information of a surgical instrument in a space inside the body of the surgical subject. That is, upon applying the motion information obtained through the virtual body model to the body of the surgical subject, the computer may derive the type of the optimized operation unit and the structure of the optimized arm part.

In an embodiment, the computer may obtain the motion information of the operation unit by simulating the surgical operation through the virtual body model, using only the operation unit of the surgical instrument. The computer may determine the type of the optimized operation unit, with which the surgical operation is applied to the surgical target site of the surgical subject, based on the motion information of the operation unit. For example, the computer may analyze motion information of the operation unit to grasp motion pattern information about the surgical operation performed by the operation unit. When the surgical operation performed by the operation unit is a cropping operation, the computer may recognize that the surgical operation is the cropping operation, from the motion pattern information and may derive the kind (type) of the operation unit suitable for cropping. Also, even when the same surgical operation is performed, the movement of the operation unit may be different depending on the type of surgery or the target site of surgery. In this case, the computer may analyze the motion pattern information of the operation unit to derive the type of operation unit that is most suitable for the corresponding surgery or the corresponding surgical site.

In addition, the computer may obtain the inner body information and body surface information of the surgical subject, and thus may determine the structure of the arm part. The inner body information includes information about the placement state of organs located in the inner body space of the surgical subject; the body surface information may include body surface shape information of the surgical subject.

The computer may obtain the inner body information and the body surface information in various manners. In an embodiment, the inner body information or the body surface information may be obtained from the virtual body model generated by applying medical image data for a patient to a pneumoperitoneum formation algorithm. The pneumoperitoneum formation algorithm refers to an algorithm for generating 3D modeling data in a normal state into 3D modeling data in a pneumoperitoneum state.

Unlike normal open surgery, when laparoscopic surgery or robot surgery is performed, gas (i.e., carbon dioxide pneumoperitoneum) is injected into the body and then the patient's body is formed to be in a pneumoperitoneum state, to form a space where a surgical instrument moves inside the body. That is, when a patient is the target of laparoscopic surgery or robot surgery, there is a need for a modeling process in the pneumoperitoneum state such that the medical staff performs simulation through the same virtual body model as the patient's body in actual surgery. The computer obtains body surface information from the patient's body surface in a virtual body model formed in the pneumoperitoneum state, by applying the pneumoperitoneum formation algorithm, and then obtains inner body information by extracting organ placement information inside the body.

In an embodiment, upon determining the structure of the arm part, the computer may calculate the operation range of the arm part from the inner body information and body surface information of the surgical subject, and may derive the placement relationship between the arm part and the operation unit based on the operation range of the arm part. The computer may determine at least one of the length of the arm part, whether there is a joint part, and motion information of the joint part depending on the placement relationship with the operation unit. At this time, the operation range of the arm part refers to the range in which the arm part is capable of being operated depending on the motion of the operation unit based on the inner body information and body surface information of the surgical subject.

For example, the computer may grasp the organ placement state from the inner body information of the surgical subject, and thus the computer may determine whether organs are affected when the movement of the arm part occurs depending on the movement of the operation unit. Accordingly, the computer may calculate the operation range of the arm part capable of performing the operation without affecting the organ. Furthermore, the computer may derive the placement relationship between the arm part and the operation unit, based on the placement of the internal organs of the surgical subject or the position relationship with shapes of the body surface within the operation range of the arm part. That is, the computer may determine the structure of the optimized arm part based on the placement relationship with the operation unit within the operation range of the arm part. For example, the computer may calculate the placement relationship such as the angle, degree of slope, and degree of bending between the operation unit and the arm. The computer may determine whether a joint part is required at the arm part, based on the placement relationship. The joint part may connect the operation unit to the arm part; alternatively, when the arm part includes a plurality of arms, the joint part may be a part connecting an arm to an arm. When the arm part includes a joint part, the computer may determine the degree of motion such as the number of joints, the degree of freedom of a joint, the angle of rotation, and the degree of bending, or the like.

In an embodiment of the inventive concept, upon deriving a configuration of the surgical instrument, the computer may obtain the optimal entry position on the body surface of the surgical subject into which the surgical instrument is inserted, and may determine the configuration of the surgical instrument in consideration of the optimal entry position. At this time, the computer may use a predetermined entry position or may obtain an optimal entry position by performing the method of FIG. 4 to be described later. In an embodiment, when inserting a surgical instrument into the optimal entry position, the computer may derive the structure of the arm part capable of being inserted without affecting organs inside a body or the shape of a body surface. For example, it is possible to derive the length of the arm part, whether there is a joint part, motion information of the joint part, and the like.

Figure 9:
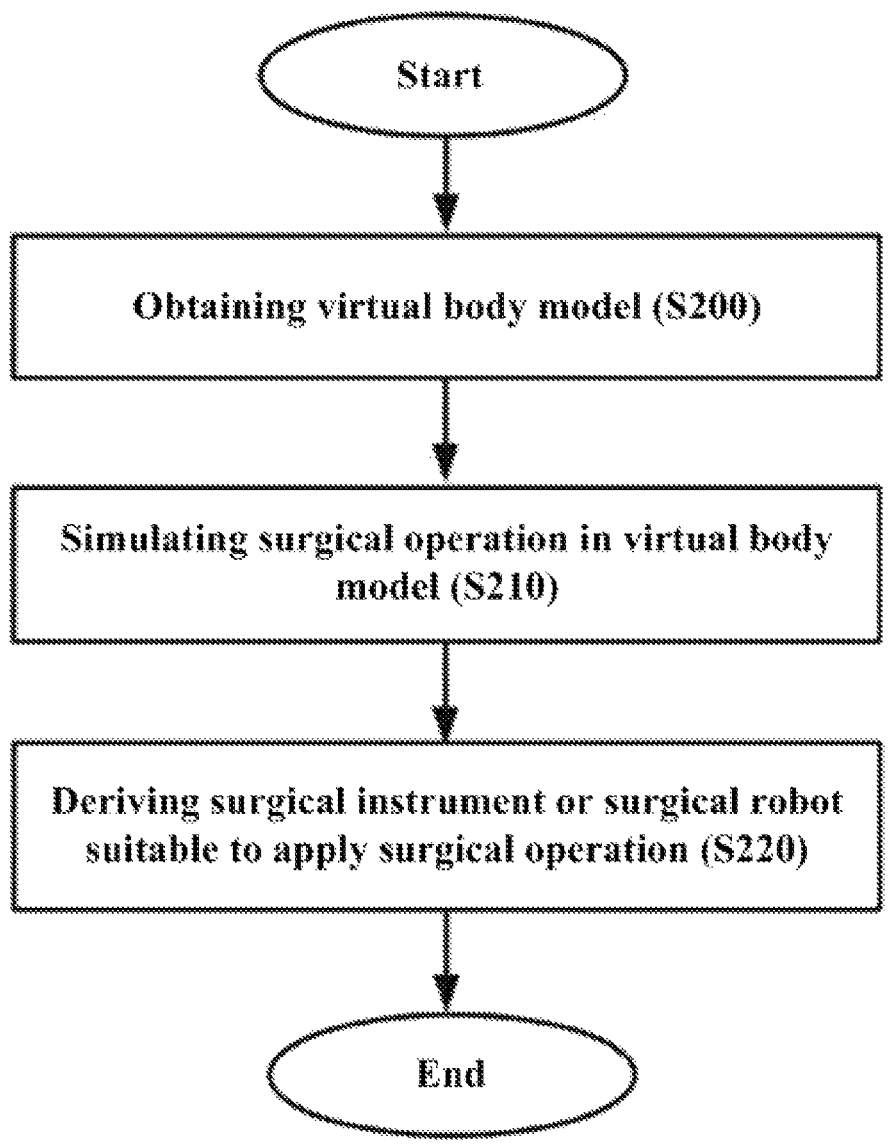
FIG. 9 is a flowchart schematically illustrating a method for providing an optimized surgical instrument, according to another embodiment of the inventive concept.

FIG. 9 is a flowchart schematically illustrating a method for providing an optimized surgical instrument according to another embodiment of the inventive concept.

Each of the steps illustrated in FIG. 9 may be performed in a time-series manner in the server 100 or controller 30 illustrated in FIG. 7. Alternatively, each of the steps may be performed in a computing device provided separately. Hereinafter, for convenience of description, each step may be described as being performed by a computer. However, the subject of each step is not limited to a specific device. All or part of steps may be performed by the server 100 or the controller 30, or may be performed on a separately-provided computing device.

Referring to FIG. 9, a method for providing an optimized surgical instrument performed by a computer according to an embodiment of the inventive concept may include obtaining a virtual body model generated to be matched with the body state of a surgical subject (S200), simulating a surgical operation corresponding to an actual surgical operation of a surgical subject in the virtual body model (S210), and deriving a surgical instrument or surgical robot suitable to apply a surgical operation in the inner body space of the surgical subject based on the simulation result (S220). Hereinafter, the detailed description of each operation is provided.

The computer may obtain a virtual body model generated to be matched with the body state of a surgical subject (S200). This may be performed in the same manner as step S100 of FIG. 8 described above, and thus a detailed description is omitted here.

The computer may simulate the surgical operation corresponding to the actual surgical operation of the surgical subject in the virtual body model (S210). This may be performed in the same manner as step S110 of FIG. 8 described above, and thus a detailed description is omitted here.

The computer may derive a surgical instrument or surgical robot suitable to apply a surgical operation in the inner body space of the surgical subject based on the simulation result (S220).

In an embodiment, the computer may obtain motion information of the surgical instrument from the simulation result and may analyze the surgical operation from the motion information. The computer may determine the type of surgical robot optimized for the surgical subject or the type of surgical instrument included in a specific surgical robot, based on the analyzed surgical operation.

That is, there may be various types of surgical robots depending on the type of surgery, the body feature of the surgical subject, or the like; each company may have a different type of surgical robot. Accordingly, in the inventive concept, it is possible to obtain the motion information of the surgical instrument through the virtual body model, to derive the type of surgical robot that is most suitable for the surgical operation, and to recommend the type of surgical robot to the medical staff. In addition, the motion feature of the surgical instrument may be different for each surgical robot; there may be differences in the types of surgical instruments held by a surgical robot of each company. Accordingly, in the inventive concept, it is possible to determine a specific surgical robot optimized to implement the movement of the surgical instrument obtained through the virtual body model. Moreover, because one surgical robot may include several surgical instruments performing the same surgical operation, the computer may determine a specific surgical instrument optimized to implement the movement of the surgical instrument obtained through the virtual body model among various surgical instruments in a specific surgical robot.

In an embodiment of the inventive concept, upon deriving a surgical instrument or surgical robot, the computer may obtain the optimal entry position on the body surface of the surgical subject into which the surgical instrument is inserted, and may determine the surgical instrument or surgical robot in consideration of the optimal entry position. At this time, the computer may use a predetermined entry position or may obtain an optimal entry position by performing the method of FIG. 10 to be described later. In an embodiment, the computer may derive the surgical instrument capable of being inserted without affecting organs inside a body or the shape of a body surface, or the surgical robot including the corresponding surgical instrument when inserting a surgical instrument into the optimal entry position.

In addition, in an embodiment of the inventive concept, the computer may record and store the movement of the surgical instrument in real time during surgery. As described above, the computer may determine at least one optimal surgical instrument based on the simulation result, and a user may select one surgical instrument among the determined surgical instrument. At this time, the computer may simulate the surgical procedure again, using the surgical instrument selected from the user. In this way, it is possible to derive an optimized actual surgical procedure (i.e., an actual surgical operation).

Figure 10:
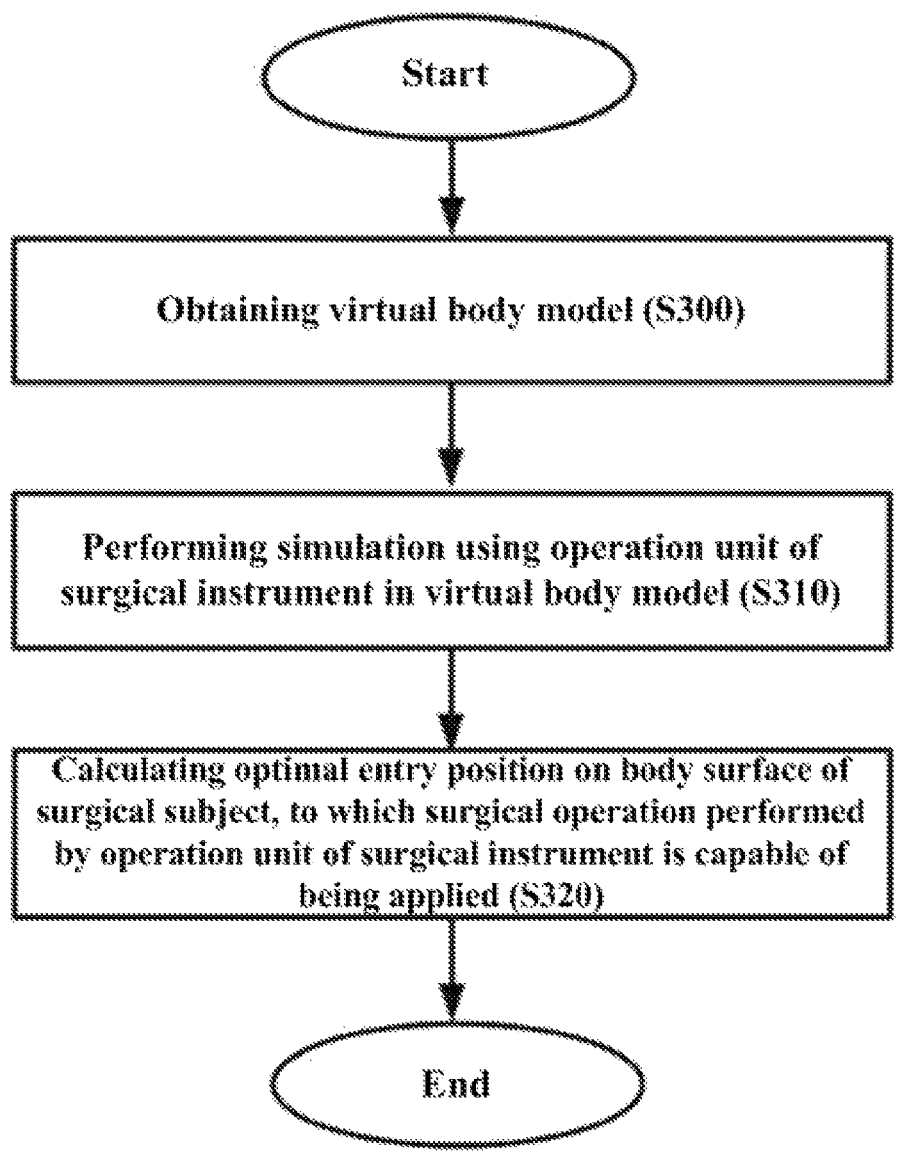
FIG. 10 is a flowchart schematically illustrating a method for providing an optimal entry position of a surgical instrument according to an embodiment of the inventive concept.

FIG. 10 is a flowchart schematically illustrating a method for providing an optimal entry position of a surgical instrument according to an embodiment of the inventive concept.

Each of the steps illustrated in FIG. 10 may be performed in a time-series manner in the server 100 or controller 30 illustrated in FIG. 7. Alternatively, each of the steps may be performed in a computing device provided separately. Hereinafter, for convenience of description, each step may be described as being performed by a computer. However, the subject of each step is not limited to a specific device. All or part of steps may be performed by the server 100 or the controller 30, or may be performed on a separately-provided computing device.

Referring to FIG. 10, a method for providing an optimal entry position of a surgical instrument performed by a computer according to an embodiment of the inventive concept may include obtaining a virtual body model generated to be matched with a body state of a surgical subject (S300), performing simulation using an operation unit of a surgical instrument for performing a surgical operation on a surgical target site of the surgical subject in the virtual body model (S310), and calculating the optimal entry position on the body surface of the surgical subject, to which the surgical operation performed by the operation unit is capable of being applied in the inner body space of the surgical subject based on the simulation result (S320). Hereinafter, the detailed description of each operation is provided.

The computer may obtain a virtual body model generated to be matched with the body state of a surgical subject (S300). This may be performed in the same manner as step S100 of FIG. 8 described above, and thus a detailed description is omitted here.

The computer performs simulation using an operation unit of a surgical instrument for performing a surgical operation on a surgical target site of the surgical subject in the virtual body model (S310). This may be performed in the same manner as step S110 of FIG. 8 described above, and thus a redundant description is omitted.

In an embodiment, the computer may simulate a surgical operation for the surgical target site in the virtual body model, using only the operation unit without considering the configuration of the arm part where a motion occurs depending on the surgical operation of the operation unit. The computer may obtain motion information of the operation unit from the simulation result. At this time, as described above, the motion information may be information indicating a position change of the surgical instrument generated as a surgical operation is performed; for example, the motion information may be the set of coordinate values indicating the position of each point of the surgical instrument on coordinates of the virtual body model.

Accordingly, in such the simulation, virtual surgery may be performed using only the operation unit of the surgical instrument in the virtual body model without considering whether the internal organs of the body is affected, the entry position on the patient's body surface, or the like depending on the feature of the arm part of the surgical instrument or the operation of the arm part, thereby applying the easiest and most familiar surgical operation pattern.

The computer may calculate the optimal entry position on the body surface of the surgical subject, to which the surgical operation performed by the operation unit is capable of being applied in the inner body space of the surgical subject based on the simulation result (S320).

In an embodiment, the computer may extract an enterable range from the body surface of the surgical subject, to which the motion information of the operation unit is capable of being applied in the inner body space of the surgical subject. Also, the computer may calculate the optimal entry position from the enterable range by reflecting the operation range of the arm part where a motion occurs depending on the surgical operation of the operation unit.

For example, the computer may extract the enterable range capable of applying motion information of the operation unit on the entire body surface of the surgical subject. For example, the enterable range may be a location on the body surface other than i) an area where the operation unit of the surgical instrument may not be reached when the surgical operation is performed, or ii) an area corresponding to a case where the operation unit of the surgical instrument reaching a specific point may not perform the specific surgical operation. For another example, the enterable range may be calculated based on the function of a surgical instrument. For example, there is a gripping function, a cutting function, and a searing function (hemostasis function) depending on the type of surgical instrument; different surgical instruments are used for each function. Alternatively, a single surgical instrument (e.g., Harmonic ACE) may also perform all functions. Accordingly, the computer may extract an enterable range capable of applying motion information of the operation unit according to each function based on the function of the surgical instrument.

Furthermore, the computer may derive the optimal entry position by calculating a specific area or specific point that satisfies the operation range of the arm part within the extracted enterable range of the body surface. That is, when the operation unit is moved, the arm part connected to the operation unit is also moved. At this time, because the computer has obtained the simulation result in a state of expressing only the operation unit through the virtual body model, the computer needs to calculate the optimal entry position by additionally considering the motion of the arm part.

For example, the computer may calculate an operation range in which the arm part may operate at maximum while the arm part does not affect the organ or body surface based on the inner body information (i.e., an organ placement state inside the body) and body surface information (i.e., a body surface shape state) of the surgical subject. The computer may determine the optimal entry position that does not affect the motion of the surgical instrument in the inner body space, by reflecting the operation range within the enterable range of the body surface.

Furthermore, in an embodiment of the inventive concept, the computer may derive the configuration of a surgical instrument suitable to perform a surgical operation by inserting a surgical instrument into the optimal entry position. Because a process of deriving an optimal surgical instrument has been described in detail through the embodiments of FIGS. 8 and 9, the description will be omitted in this embodiment.

In the meantime, in the above-described embodiments, for convenience of description, the number of surgical instruments is described without consideration. However, the inventive concept is not limited thereto. The same process may be applied to each surgical instrument even when surgery is performed while a plurality of surgical instruments are included.

For example, when a tool A, a tool B, and a tool C are used during surgical robot or laparoscopic surgery, the computer may exclude an area (i.e., the body surface area where there is a point where the operation unit is not able to be reached due to the length limitation of the surgical instrument when the surgical operation is performed), where the operation unit of the tool A is not able to be reached when a surgical operation is perform, from the enterable range. Besides, in a process of performing a surgical operation by entering the tool A, the computer may exclude a body surface area that collides with body organs or tissues, from the enterable range. Furthermore, after the surgical instrument enters each body surface point within the enterable range, when the computer fails to implement the surgical operation required at a specific location, the computer may exclude the corresponding body surface point from the enterable range. In this way, the computer may calculate the enterable range for the tool A. The computer may individually perform the process of calculating the enterable range on each surgical instrument (e.g., the tool B and the tool C) to calculate the optimal entry position of each surgical instrument. Moreover, as described above, the computer may individually perform the process of calculating the enterable range on each function based on the function of the surgical instrument and then may also calculate the optimal entry position to which the function of each surgical instrument may be applied.

For another example, when a plurality of surgical instruments need to be entered into a single optimal entry position, after extracting the optimal entry range for each surgical instrument, the computer may determine a range where a plurality of optimal entry ranges overlap with one another, as an optimal entry position. For example, when the tool A is changed to the tool D in a process of performing surgery, the computer may calculate the overlapping area of the enterable range for the tool A and the enterable range for the tool D, as an optimal entry position candidate area. Because a position at which the surgical instrument is capable of being entered is limited to the specific number (e.g., 3), the same entry position needs to be used when the tool A is changed to the tool D, and thus the computer may determine the position that satisfies both the enterable range of the tool A and the enterable range of the tool D, as the final optimal entry position.

For another example, in the case where the same surgical instrument is used multiple times within the virtual body model, because it may be difficult to perform all surgical operations in a single surgical instrument entry position when a range (i.e., the range of motion) where a surgical operation of the surgical instrument is performed is wide, the computer may divide a range (i.e., the range of motion) where the surgical instrument is used, into several groups reachable from a plurality of entry positions on the body surface. For example, when performing laparoscopic surgery or robot surgery by generating three entry positions on the body surface, the computer divides the motion range of a surgical instrument into groups of 3 or less. At this time, the computer divides the range of motion based on whether it is possible to be reached from a plurality of enterable ranges selected by other surgical instruments. Furthermore, when a specific surgical instrument (i.e., the first surgical instrument) with a wide range of motion is used simultaneously with another surgical instrument (i.e., the second surgical instrument) and the optimal entry position to which the other surgical instrument (i.e., the second surgical instrument) is essentially entered is determined, the computer may set the motion range of the first surgical instrument, at a point in time when the first surgical instrument is used with the second surgical instrument, as the range in which the first surgical instrument is incapable of being accessed through the optimal entry position (i.e., the keyhole into which the second surgical instrument is entered) of the second surgical instrument. Also, when the first surgical instrument is used continuously in spite of the change to another surgical instrument, the computer may set a group that an operation needs to be performed by entering the same entry position, in consideration of the convenience while surgery is performed on a user, and a time required for surgery.

For another example, in a process of calculating the entry positions of one or more surgical instruments, the computer may exclude a camera entry range and an assist tool entry range from the enterable range of the body surface of a patient. For example, a camera is entered through an area around a navel to capture the interior of the entire abdomen of the patient through movement. To this end, the computer may perform a process of reducing an enterable range after excluding an area around the navel from the initially-set enterable range.

In an embodiment, the computer may perform a process of calculating one or more optimal entry positions, using a Monte Carlo Method when a plurality of surgical instruments are used.

As described above, according to an embodiment of the inventive concept, the optimal entry position of the surgical instrument may be determined by reflecting the results of a surgical simulation performed by the medical staff without considering the entry position of a surgical instrument and contacting the arm part of the surgical instrument with organs, and thus allowing medical staff to perform the most convenient surgical operation.

Furthermore, according to an embodiment of the inventive concept, as the optimal entry position optimized for a patient's physical condition is used without using the general surgical instrument entry position, the medical staff may prevent the execution of a specific operation from being restricted in an actual surgical procedure due to a patient's organ placement characteristics or a length of a surgical instrument.

Also, according to an embodiment of the inventive concept, when surgery is performed using all surgical instruments used in surgery at the specific number of surgical instrument entry positions, several surgical instrument entry positions optimized for all surgical instruments may be determined. Moreover, it is possible to accurately set an entry position, which each surgical instrument needs to enter, among the specific number of optimal entry positions.

Moreover, according to an embodiment of the inventive concept, when a plurality of surgical robots or a plurality of surgical instruments performing the same action in a specific surgical robot may be used, it may be possible to allow medical staff to perform efficient and rapid surgery by proposing a surgical robot or surgical instrument that is most suitable for the patient's physical condition and the surgical operation of the medical staff.

In addition, according to an embodiment of the inventive concept, when the surgical robot performs surgery by itself, the optimized surgery may be performed through calculating the optimal entry position of each surgical instrument.

Also, according to an embodiment of the inventive concept, the surgical instrument with the optimal structure may be determined by reflecting the results of a surgical simulation performed by the medical staff without considering the entry position of a surgical instrument and contacting the arm part of the surgical instrument with organs, and thus the medical staff may conveniently operate surgical instruments depending on the surgical operation pattern of the medical staff. Accordingly, the entire surgical procedure may be effectively performed, thereby reducing surgical errors.

Moreover, according to an embodiment of the inventive concept, as surgery is performed using an optimized surgical instrument, the medical staff may prevent the execution of a specific surgical operation from being restricted in an actual surgical procedure due to a patient's organ placement characteristics or a length of a surgical instrument.

Figure 11:
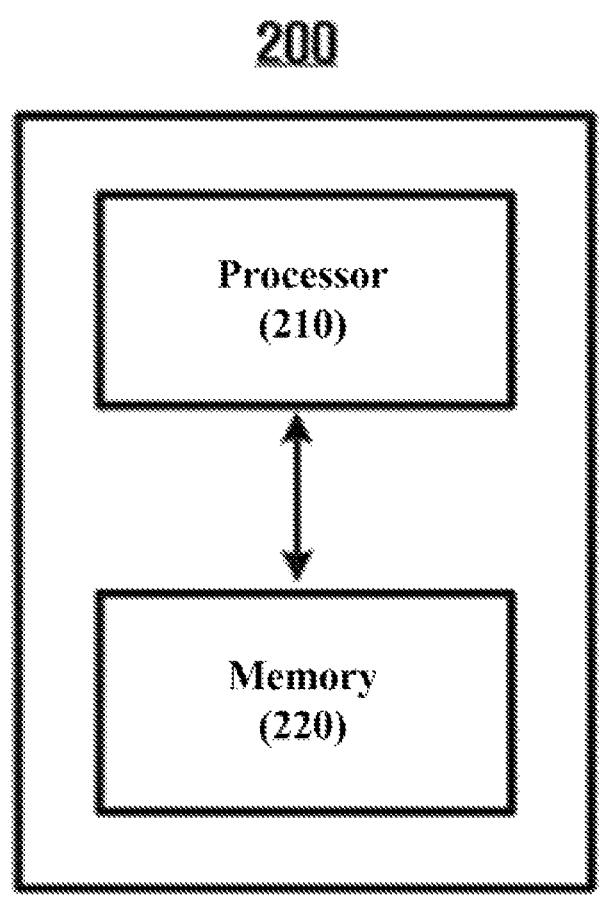
FIG. 11 is a diagram schematically illustrating a configuration of a device 200 performing an optimized surgical instrument providing method or a method for providing an optimal entry position of a surgical instrument, according to an embodiment of the inventive concept.

FIG. 11 is a diagram schematically illustrating a configuration of a device 200 performing an optimized surgical instrument providing method or a method for providing an optimal entry position of a surgical instrument, according to an embodiment of the inventive concept.

Referring to FIG. 11, a processor 210 may include one or more cores (not illustrated), a graphic processing unit (not illustrated), and/or a connection path (e.g., a bus, or the like) through which a signal is transmitted and received with other components.

According to an embodiment, the processor 210 performs an optimized surgical instrument providing method or an optimal entry position providing method of a surgical instrument, which is described with reference to FIGS. 8 to 10, by executing one or more instructions stored in a memory 220.

For example, the processor 210 obtains a virtual body model generated to be matched with the body state of a surgical subject, simulates a surgical operation using a surgical instrument in a virtual body model, and derives a configuration of a surgical instrument suitable to apply a surgical operation performed by a surgical instrument in a space inside the body of the surgical subject based on the simulation result, by executing one or more instructions stored in the memory 220.

For another example, the processor 210 obtains a virtual body model generated to be matched with the body state of a surgical subject, simulates a surgical operation corresponding to an actual surgical operation of a surgical subject in the virtual body model, and derives a surgical instrument or surgical robot suitable to apply a surgical operation in the inner body space of the surgical subject based on the simulation result, by executing one or more instructions stored in the memory 220.

For still another example, the processor 210 obtains a virtual body model generated to be matched with a body state of a surgical subject, performs simulation using an operation unit of a surgical instrument for performing a surgical operation on a surgical target site of the surgical subject in the virtual body model, and calculates the optimal entry position on the body surface of the surgical subject, to which the surgical operation performed by the operation unit is capable of being applied in the inner body space of the surgical subject based on the simulation result, by executing one or more instructions stored in the memory 220.

In the meantime, the processor 210 may further include Random Access Memory (RAM) (not illustrated) and Read-Only Memory (ROM) (not illustrated) that temporarily and/or permanently store a signal (or data) processed inside the processor 210. Furthermore, the processor 210 may be implemented in the form of a system on chip (SoC) including at least one of a graphic processor, RAM, and ROM.

Programs (one or more instructions) for the processing and controlling of the processor 210 may be stored in the memory 220. The programs stored in the memory 220 may be divided into a plurality of modules depending on functions.

The method for providing an optimal surgical instrument or the method for providing an optimal entry position of a surgical instrument according to an exemplary embodiment of the inventive concept may be implemented by a program (or an application) and may be stored in a medium such that the program is executed in combination with a computer being hardware.

In the meantime, in the above-described embodiments of the inventive concept, a program may include a code encoded by using a computer language such as C, C++, JAVA, a machine language, or the like, which a processor (CPU) of the computer may read through the device interface of the computer, such that the computer reads the program and performs the methods implemented with the program. The code may include a functional code related to a function that defines necessary functions that execute the method, and the functions may include an execution procedure related control code necessary for the processor of the computer to execute the functions in its procedures. Further, the code may further include additional information that is necessary for the processor of the computer to execute the functions or a memory reference related code on which location (address) of an internal or external memory of the computer should be referenced by the media. Moreover, when the processor of the computer needs to communicate with any other remote computer or any other remote server to perform the functions, the code may further include a communication-related code associated with how to communicate with any other remote computer or server using the communication module of the computer, what information or media should be transmitted or received during communication, or the like.

The stored medium refers not to a medium, such as a register, a cache, or a memory, which stores data for a short time but to a medium that stores data semi-permanently and is read by a device. Specifically, for example, the stored media include, but are not limited to, ROM, RAM, CD-ROM, magnetic tape, floppy disk, optical data storage device, and the like. That is, the program may be stored in various recording media on various servers that the computer can access, or various recording media on the computer of the user. In addition, the media may be distributed to a computer system connected to a network, and a computer-readable code may be stored in a distributed manner.

The steps of a method or algorithm described in connection with the embodiments of the inventive concept may be embodied directly in hardware, in a software module executed by hardware, or in a combination thereof. The software module may reside on a Random Access Memory (RAM), a Read Only Memory (ROM), an Erasable Programmable ROM (EPROM), an Electrically Erasable Programmable ROM (EEPROM), a Flash memory, a hard disk, a removable disk, a CD-ROM, or a computer readable recording medium in any form known in the art to which the inventive concept pertains.

Although embodiments of the inventive concept have been described herein with reference to accompanying drawings, it should be understood by those skilled in the art that the inventive concept may be embodied in other specific forms without departing from the spirit or essential features thereof. Therefore, the above-described embodiments are exemplary in all aspects, and should be construed not to be restrictive.

According to an embodiment of the inventive concept, it is possible to derive an improved surgical procedure compared to the surgical process performed in the actual surgical procedure, by applying a genetic algorithm.

According to an embodiment of the inventive concept, surgical cue sheet data including the optimized surgical procedure may be derived through a genetic algorithm, and thus the surgical cue sheet data may be provided to actual medical staff. In addition, actual medical staff may utilize the optimized surgical cue sheet data during actual surgery, thereby performing accurate surgical operations and surgical procedures.

According to an embodiment of the inventive concept, surgical cue sheet data including the optimized surgical procedure may be derived through a genetic algorithm, and thus the surgical cue sheet data may be used as learning data in a learning process such as deep learning.

According to an embodiment of the inventive concept, the optimal entry position of the surgical instrument may be determined by reflecting the results of a surgical simulation performed by the medical staff without considering the entry position of a surgical instrument and contacting the arm part of the surgical instrument with organs, and thus allowing medical staff to perform the most convenient surgical operation.

According to an embodiment of the inventive concept, as the optimal entry position optimized for a patient's physical condition is used without using the general surgical instrument entry position, the medical staff may prevent the execution of a specific operation from being restricted in an actual surgical procedure due to a patient's organ placement characteristics or a length of a surgical instrument.

According to an embodiment of the inventive concept, when surgery is performed using all surgical instruments used in surgery at the specific number of surgical instrument entry positions, several surgical instrument entry positions optimized for all surgical instruments may be determined. Moreover, it is possible to accurately set an entry position, which each surgical instrument needs to enter, among the specific number of optimal entry positions. In addition, it is possible to minimize the number of entry positions to be entered depending on the type of a surgical instrument as well as the entry position. Accordingly, it may be possible to reduce a patient's surgical scar.

According to an embodiment of the inventive concept, when a plurality of surgical robots or a plurality of surgical instruments performing the same action in a specific surgical robot may be used, it may be possible to allow medical staff to perform efficient and rapid surgery by proposing a surgical robot or surgical instrument that is most suitable for the patient's physical condition and the surgical operation of the medical staff.

According to an embodiment of the inventive concept, when the surgical robot performs surgery by itself, the optimized surgery may be performed through calculating the optimal entry position of each surgical instrument.

According to an embodiment of the inventive concept, the surgical instrument with the optimal structure may be determined by reflecting the results of a surgical simulation performed by the medical staff without considering the entry position of a surgical instrument and contacting the arm part of the surgical instrument with organs, and thus the medical staff may conveniently operate surgical instruments depending on the surgical operation pattern of the medical staff. Accordingly, the entire surgical procedure may be effectively performed, thereby reducing surgical errors.

According to an embodiment of the inventive concept, as surgery is performed using an optimized surgical instrument, the medical staff may prevent the execution of a specific surgical operation from being restricted in an actual surgical procedure due to a patient's organ placement characteristics or a length of a surgical instrument.

The effects of the present inventive concept are not limited to the aforementioned effects, and other effects not mentioned herein will be clearly understood from the following description by those skilled in the art to which the inventive concept pertains.

While the inventive concept has been described with reference to exemplary embodiments, it will be apparent to those skilled in the art that various changes and modifications may be made without departing from the spirit and scope of the inventive concept. Therefore, it should be understood that the above embodiments are not limiting, but illustrative.

What is claimed is:

1. An optimized surgical instrument providing method performed by a computer, the method comprising:
    obtaining a virtual body model generated to be matched with a body state of a surgical subject;
    obtaining inner body information and body surface information of the surgical subject,
    wherein the inner body information includes information about a placement state of organs located in an inner body space of the surgical subject, and the body surface information includes body surface shape information of the surgical subject, and
    wherein the inner body information and the body surface information are obtained from the virtual body model generated by applying medical image data for a patient to a pneumoperitoneum formation algorithm that is an algorithm for generating 3D modeling data in a normal state into 3D modeling data in a pneumoperitoneum state;
    simulating a surgical operation within the virtual body model, using a surgical instrument having an arm part and an operation unit;
    calculating, based on the simulation result, an operation range of the arm part,
    wherein the operation range of the arm part is a range in which the arm part is capable of being operated depending on a motion of the operation unit without affecting the organs of the surgical subject, based on the inner body information and the body surface information of the surgical subject; and
    determining, based on the calculation result, a structure of the surgical instrument by determining a length of the arm part, an existence of a joint part that connects the operation unit to the arm part, and motion information of the joint part depending on a placement relationship of the joint part with the operation unit.

2. The method of claim 1, further comprising:
    obtaining an optimal entry position on a body surface of the surgical subject into which the surgical instrument is inserted,
    wherein the determining comprises:
    determining the structure of the surgical instrument in consideration of the optimal entry position.

3. An optimal entry position providing method of a surgical instrument performed by a computer, the method comprising:
    obtaining a virtual body model generated to be matched with a body state of a surgical subject;
    obtaining inner body information and body surface information of the surgical subject,
    wherein the inner body information includes information about a placement state of organs located in an inner body space of the surgical subject, and the body surface information includes body surface shape information of the surgical subject, and
    wherein the inner body information and the body surface information are obtained from the virtual body model generated by applying medical image data for a patient to a pneumoperitoneum formation algorithm that is an algorithm for generating 3D modeling data in a normal state into 3D modeling data in a pneumoperitoneum state;
    performing simulation using an operation unit of a surgical instrument having an arm part and an operation unit, for performing a surgical operation on a surgical target site of the surgical subject in the virtual body model; and
    calculating, based on the simulation result, an optimal entry position on a body surface of the surgical subject, to which the surgical operation performed by the operation unit is capable of being applied in an inner body space of the surgical subject.

4. The method of claim 3, wherein the performing of the simulation includes:
    obtaining motion information of the operation unit upon simulating a surgical operation for the surgical target site in the virtual body model, using the operation unit without considering a configuration of an arm part where a motion occurs depending on the surgical operation of the operation unit.

5. The method of claim 4, wherein the calculating of the optimal entry position includes:
    extracting an enterable range from the body surface of the surgical subject, to which the motion information of the operation unit is capable of being applied in the inner body space of the surgical subject; and calculating the optimal entry position from the enterable range by reflecting an operation range of the arm part where a motion occurs depending on the surgical operation of the operation unit.

6. The method of claim 5, wherein the operation range of the arm part is a range in which the arm part is capable of being operated depending on the motion of the operation unit based on inner body information and body surface information of the surgical subject,
wherein the inner body information includes information about a placement state of an organ positioned in the inner body space of the surgical subject, and
wherein the body surface information includes body surface shape information of the surgical subject.

7. The method of claim 3, further comprising:
deriving a configuration of the surgical instrument suitable to perform the surgical operation by inserting the surgical instrument into the optimal entry position.

8. The method of claim 1, further comprising:
simulating the surgical operation within the virtual body model, using a surgical robot having a plurality of surgical instruments; and
determining, based on the simulation result, a type of the surgical robot optimized for the surgical subject.

9. The method of claim 8, further comprising:
obtaining an optimal entry position on a body surface of the surgical subject into which the surgical instrument is inserted; and
determining the type of the surgical robot in consideration of the optimal entry position.

* * * * *